United States Patent [19]

Hillegas et al.

[11] Patent Number: 4,994,388

[45] Date of Patent: Feb. 19, 1991

[54] COLLAGEN-COATED POLYSTYRENE MICROCARRIER BEADS

[75] Inventors: William J. Hillegas; James Varani; David L. Helmreich, all of Ann Arbor,, Mich.

[73] Assignees: Solohill Engineering, Inc.; The University of Michigan, both of Ann Arbor,, Mich.

[21] Appl. No.: 181,853

[22] Filed: Apr. 15, 1988

[51] Int. Cl.$^5$ .............................................. C12N 5/00
[52] U.S. Cl. .............................. 435/240.243; 435/178; 435/180; 435/181; 435/182; 435/240.24; 435/240.25
[58] Field of Search ............... 435/284, 285, 286, 297, 435/300, 301, 178, 180, 181, 240.24, 240.243

[56] References Cited

U.S. PATENT DOCUMENTS

| | | | |
|---|---|---|---|
| 3,997,396 | 12/1976 | Delente | 435/285 X |
| 4,287,305 | 9/1981 | Compere et al. | 435/180 X |
| 4,373,027 | 2/1983 | Berneman et al. | 435/240 |
| 4,448,884 | 5/1984 | Henderson | 435/240.24 |
| 4,734,373 | 3/1988 | Bartal | 435/301 X |

OTHER PUBLICATIONS

Jacobson et al., Tissue and Cell, vol. 14, No. 1 (1982), pp. 69–83.
Biological Abstracts, vol. 75, No. 1, Jan. 1, 1983, Abstract No. 1557, Jacobson et al.
Biological Abstracts, vol. 76, No. 6, Sep. 15, 1983, Abstract No. 45711, Pierschbacher et al.
Biological Abstracts, vol. 81, No. 5, Mar. 1, 1986, Abstract No. 40846, Schwarz et al.
Biological Abstracts, vol. 77, No. 11, Jun. 1, 1984, Abstract No. 80863, McAbee et al.

*Primary Examiner*—Sam Rosen
*Attorney, Agent, or Firm*—Rohm & Monsanto

[57] ABSTRACT

A microcarrier bead system for culturing anchorage-dependent cells is formed of a polystyrene core with a coating of collagen fixed thereover. In certain embodiments, the coating is a protein, such as laminin or fibronectin. The microcarrier bead is of low density, illustratively 1.02 g/cc, and therefore requires less agitation of the nutrient media to maintain suspension. This reduced stirring causes lower shear forces to impinge upon the cells, thereby improving the attachment and proliferation of the cells being cultured. The microcarrier bead of the present invention exhibits surprising advantages with respect to cell attachment and harvesting over beads formed entirely of collagen, or of DEAE-dextran coated with collagen. During harvesting, contamination of the product resulting from dissolved collagen, particularly when proteolytic enzymes are used, is minimized. Additionally, adsorption of toxins and product by the subject microcarrier beads is minimized.

14 Claims, No Drawings

COLLAGEN-COATED POLYSTYRENE MICROCARRIER BEADS

BACKGROUND OF THE INVENTION

This invention relates generally to systems for culturing cells, and more particularly, to a collagen-coated polystyrene microcarrier bead system which serves as a microcarrier support for the culturing of anchorage-dependent cells.

The use of carrier support systems to facilitate growth of biological cells is long and varied in its history. Early systems for effecting such cell growth in usable quantities have included the well-known petri dish and flasks. Efforts intended to increase the quantity of cell production have resulted in the use of large trays; the overall effect achieved being the increase in the size of the surface on which the biological cells are grown, specifically anchorage-dependent cells. Some of these early cell-growth systems are still in use for applications where small-scale production will suffice, such as in hospital and university research units.

The state of the cell culturing art has continued to develop to the present day where there is an acute need for large scale commercial cell culturing systems which can achieve high rates of production. Ideally, the production rate should be flexible to accommodate batch and single-order production.

At present, the cell culturing system which enjoys utilization in some 90% to 95% of the commercial market is the roller bottle system. Essentially, a roller bottle is a cylindrical container which is arranged to contain a small amount of nutrient media. In operation, the roller bottle is rotated slowly, at about 1 to 3 rpm, whereby the nutrient media is continually caused to wet the entire interior surface of the bottle, on which cell growth is achieved. A plurality of such roller bottles are operated on a roller rack, the specific number thus rotated being responsive to the desired rate of overall cell production.

The remaining 5% to 10% of the commercial large-scale market utilizes microcarrier systems. Although other techniques have been introduced in recent years, including hollow fibers, fiber bundles, and channeled ceramic cores, only microcarrier systems have the potential for scale-up within a given reactor to achieve anchorage-dependent cell growth at commercially advantageous production rates and volumes. Scale-up in this manner is superior to scale-up by replication, as is the case with roller bottles and other known systems. In addition, microcarrier bioreactor systems are well-suited for automation systems and controlled large-scale cultivation of anchorage-dependent cells.

As is evident from Table 1, below, several microcarrier systems are presently commercially available. This table summarizes some of the characteristics of the commercially available microcarriers, including polystyrene, glass-coated polystyrene, and the novel collagen-coated polystyrene microcarriers of the present invention.

TABLE 1

| CHEMICAL COMPOSITION | BEAD DENSITY g/cc | REUSABLE | BEAD SIZE μm | SURFACE AREA cm/g | MANUFACTURER AND COUNTRY |
|---|---|---|---|---|---|
| Poly-Styrene (PS) | 1.02 | Y | 90-210 | 475 | SoloHill, USA |
| Glass-Coated PS | to | Y | 90-210 | to | SoloHill, USA |
| Collagen-Coated PS | 1.04 | N | 90-210 | 325 | SoloHill, USA |
| DEAE Dextran | 1.03 | N | 130-220 | 4-6000 | Pharmacia, Swd |
| Collagen-Coated DEAE Dextran | 1.04 | N | 100-190 | 3-5000 | Pharmacia, Swd |
| Polystyrene | 1.05 | N | 160-300 | 255 | Nunc, Denmark |
| Polystyrene | 1.05 | N | 160-230 | — | Lux, USA |
| Collagen-Coated Polyacrylamide | 1.05 | N | 160-250 | — | IBF, France |
| Collagen Gelatin | 1.04 | N | 115-230 | 3-4000 | Hazelton, USA |
| Collagen and Coated DEAE Variants | — | N | 150-250 | — | Galil, Israel |

The Swedish-based company, Pharmacia, was the first to introduce the microcarrier bead in the early 1970's. Subsequently, this company has acquired about a 90% share of the microcarrier bead market, worldwide.

The use of microcarrier beads as the microcarrier elements in anchorage-dependent cell production systems requires the availability of bioreactors, support equipment, and a stirring system. The system elements interact with one another to maintain the cell-laden microcarrier beads in suspension in the nutrient media. Much of this type of equipment is commercially available, and the effort to develop and improve bioreactor systems for use with microcarrier beads has intensified.

A problem which has significantly reduced the rate of cell production in existing systems is that of damage to the cells resulting from shear forces. During stirring, turbulence in the nutrient media impose forces upon the cells under development. The cells are so fragile that these forces both damage them and reduce their proliferation. The obvious answer to this problem is to reduce the shear forces by slowing the stirring system. However, if the potency of the stirring system is reduced too far, the microcarrier beads with their attached cells will settle and come into contact with one another and the interior walls of the container. One approach to reducing the stirring forces so that the damage to the cells being cultivated is diminished, is to decrease the density of the microcarrier beads. Microcarrier beads having lower density require less fluid turbulence to maintain them in suspension, thereby also reducing cell damage.

It is, therefore, an object of this invention to provide a simple and economical system for supporting the growth of anchorage dependent cells.

It is another object of this invention to provide a system for supporting the growth of anchorage-dependent cells which can be sterilized by standard techniques.

It is also an object of this invention to provide a microcarrier system for supporting the growth of anchorage-dependent cells.

It is a further object of this invention to provide a microcarrier system for supporting the growth of anchorage dependent cells at flexible production rates, without the need for high initial capital investment.

It is additionally an object of this invention to provide a microcarrier system which has a low density.

It is yet a further object of this invention to provide a low-density microcarrier system which can be sterilized by autoclaving methods.

It is also another object of this invention to provide a microcarrier system wherein product contamination during cell harvesting is minimized.

It is yet an additional object of this invention to provide a microcarrier system for facilitating the growth of anchorage-dependent cells wherein cell recovery is high and cell separation can easily be accomplished using proteolytic enzymes.

It is still another object of this invention to provide a microcarrier system wherein essential production features are independent of the dimensions of the microcarrier system over a broad range.

It is a yet further object of this invention to provide a microcarrier system wherein cell attachment takes place quickly.

It is also a further object of this invention to provide a microcarrier system for facilitating the growth of anchorage-dependent cells wherein absorption of culture media, products, or toxins is inhibited.

It is additionally another object of this invention to provide a microcarrier bead system which can be formed using existing laboratory methods and systems.

A still further object of this invention is to provide a microcarrier bead system which can be produced in a broad range of predetermined bead dimensions.

An additional object of this invention is to provide a microcarrier bead system wherein the manufacturing size distribution for a predetermined bead size is narrower than existing microcarrier products.

SUMMARY OF THE INVENTION

The foregoing and other objects are achieved by this invention which provides a carrier arrangement for immobilizing anchorage-dependent cells. In accordance with the invention, the arrangement is formed of a microsupport element having a core portion made of polystyrene. A surface layer portion formed of collagen is deposited to surround the core portion.

In one embodiment of the invention, the microsupport element is dimensioned between approximately 40 $\mu$m and 1000 $\mu$m, and preferably dimensioned between approximately 90 $\mu$m and 250 $\mu$m. This broad range of microcarrier bead sizes can be achieved without changing the essential production features or cell growth supporting characteristics. The inventive beads, in all sizes, are autoclavable, illustratively at 121° C for 20 minutes.

The density of the microsupport element of the present invention is approximately between 1.01 g/cc and 1.05 g/cc. Preferably, the density is approximately between 1.015 g/cc and 1.035 g/cc. Conventional polystyrene has a density of approximately 1.05 g/cc.

It is a significant characteristic of the microcarrier bead of the present invention that the composition of the polystyrene core can be modified to achieve densities on the order of 1.02 g/cc. Other available polystyrene microcarriers have a much higher density, illustratively 1.05 g/cc, and are not autoclavable. None of the presently available microcarriers, polystyrene or otherwise, have densities as low as 1.02 g/cc. As previously noted, the lower density is significant because such microcarrier beads require less vigorous agitation to maintain them in suspension in the culture medium. It must be remembered that mammalian cells in culture are quite fragile, and high shear forces are one of the major causes of low cell yield in microcarrier cultures. In fact, it has been established that density differences as small as 0.01 g/cc are significant in terms of the agitation required to keep the microcarrier bead in suspension, and correspondingly, the magnitude of the shear force exerted upon the cells.

In accordance with the invention, the surface layer portion is arranged to have integrally formed therewith a collagen coating for enhancing attachment of the anchorage-dependent cells thereto. The bead of the present invention is therefore a smooth, nonporous polystyrene bead, coated with the extracellular matrix, collagen. The source, type, and amount of collagen used to coat the beads can be varied as desired.

A highly significant feature of the microcarrier bead of the present invention is the nature of the collagen coating. There are commercially available other types of microcarriers which are provided with a collagen surface. These include a microcarrier bead formed entirely of collagen, and a further microcarrier bead made of DEAE-dextran to which collagen has covalently been linked. The results of empirical tests have revealed that the characteristics of these beads, particularly with respect to the supporting of cell attachment, cell spreading, and ultimately cell proliferation, are significantly varied from one another, and are particularly distinguishable from the microcarrier beads of the present invention.

More specifically, beads made from collagen which is covalently linked to DEAE-dextran behave similarly to those made entirely of DEAE-dextran. That is, the cells attach rapidly but do not detach readily. Such cells are therefore difficult to harvest.

In contrast to the foregoing, beads which are made entirely of collagen support the growth of some cells very well, but other cells do not proliferate well on these beads. Moreover, cell attachment to collagen beads is much slower than to the collagen-coated polystyrene microcarrier bead of the present invention.

Harvesting presents its own difficulties with collagen-only beads. Generally, harvesting from the collagen beads is achieved by dissolving the substrate in a solution of proteolytic enzymes. While this may offer advantages in some situations, it results in contamination of the soluble products by soluble fragments of collagen. Empirical testing has shown that cells attach and spread surprisingly rapidly on the collagen-coated polystyrene microcarrier beads of the present invention, and proliferate surprisingly well. Moreover, the cells can easily be harvested from the inventive microcarrier bead using proteolytic enzymes. Not only is cell recovery high, but the cells can readily be separated from the beads. Since the beads of the present invention are rigid and strong, they do not fragment easily, and therefore contamination of the culture medium is essentially eliminated.

The microsupport element is preferably in the form of a microcarrier bead, and has a softening point above 75° C. It is desirable that the softening point of the element be above 80° C., and preferably above 100° C. The softening point of conventional polystyrene is between 70-80° C.

No other microcarrier bead system offers the foregoing range of flexibility. Moreover, the nonporous nature of the microcarrier beads of the present invention inhibits absorption of culture media, products, or toxins. In addition, cell attachment to the present smooth-surfaced, collagen-coated microcarrier beads is significantly and advantageously different over the manner in which cells attach to beads made from DEAE-dextran or collagen bonded to DEAE-dextran. Test have indicated that a number of important biological processes are influenced by the substratum.

In accordance with a product-by-process aspect of the invention, a microcarrier bead is formed in accordance with the process steps of coating a polystyrene core bead with collagen, and fixing the collagen coating to the polystyrene bead. In this manner, the microcarrier bead is stable to washing and sterilization by autoclaving.

In one embodiment of the product-by-process aspect of the invention, coating of the polystyrene core bead is effected by suspending the bead in an acidic, aqueous collagen solution. The solution is evaporated to a predetermined extent to form a collagen coating over the polystyrene core bead. Although the invention can be practiced by evaporating the solution until the microcarrier bead is dry, it may be advantageous to begin the fixing process before the microcarrier bead is completely dry, but also at a point where there is no free liquid remaining. This somewhat wet state, when many microcarrier beads are being made, gives the appearance of wet sand, and commencement of the fixing process at this stage prevents clumping of the microcarrier beads.

In a specific illustrative embodiment of the invention, the acidic, aqueous collagen solution comprises 0.01 to 0.1N acetic acid. The process step of fixing the collagen coating to the microcarrier beads includes the further step of suspending the dry, coated polystyrene core bead in a buffered saline solution containing a protein cross-linking agent. In a practical embodiment, glutaraldehyde is used as the cross-linking agent.

Microcarrier bead systems represent the next generation of production methods for large-scale cultivation of cells. Microcarrier beads can be used in any application where anchorage-dependent cells are to be cultured. The largest users of these systems are manufacturers of biological products produced from animal cells grown in culture. Such products represent a large and diverse group of biologicals, which include: live virus and viral antigens for animal and human vaccines, soluble cellular products such as monoclonal antibodies, interferon and plasminogen activator, and structural cellular components, such as carcinoembryonic antigen.

DETAILED DESCRIPTION OF THE SPECIFIC ILLUSTRATIVE EMBODIMENT

In accordance with the invention, the inventive polystyrene microcarrier bead is prepared by an emulsion polymerization technique. This is a known technique, the chemistry of which can be modified by persons of ordinary skill in this art to produce a microcarrier bead having a density of approximately between 1.02 and 1.04 g/cc, and to raise its softening point to above 100° C. Normal polystyrene has a density of 1.05 g/cc and a softening point at 70-80° C.

One known technique for lowering the density of beads includes preparation of a mixture of a styrene copolymer such as styrene monomer and divinyl benzene, which is the cross-linking agent, along with density-reducing components. Such density-reducing components include, but are not limited to, t-butyl-styrene and paramethyl styrene. Practical embodiments of the invention have been produced using these components to modify the density. Both of these components have densities which are less than 1.02 g/cc. Still other components, such as detergents, may be added to the emulsion to modify the surface tension of the resulting bead.

The manufacturing technique produces beads in large quantities and in a wide, but controlled, distribution of sizes. Such beads can typically be produced in sizes of approximately between 10 and 500 μm. The beads are then classified or sieved to collect the narrow size ranges used for the microcarrier beads, which sizes are generally between 90-150 μm and 150-210 μm. This size distribution is narrower than other microcarrier products.

The installation of the collagen coating is performed in two steps; coating and fixing; the fixing step making the bead stable to washing and autoclaving. The selected core beads are suspended in an acidic, aqueous collagen solution (0.01-0.1N acetic acid), and the solution is evaporated to dryness. The dry, collagen-coated beads are then suspended in a phosphate-buffered saline solution which contains a protein cross-linking agent such as glutaraldehyde. By this technique, the collagen coating is thus crosslinked, thereby enabling subsequent use without being redissolved or rendered inactive. Thus, the microcarrier bead of the present invention can withstand immersion in culture media, washing in distilled water, and steam autoclaving. The fixed beads are then rinsed in water several times to remove the unreacted glutaraldehyde. The beads are then dried and packaged.

In an alternative embodiment of the invention, as indicated previously, the beads wetted with the collagen solution are not dried entirely before the start of the fixing step. Not only does this save time which would otherwise be spent drying the beads, but also serves to reduce the probability of bead clumping. Such clumps of beads are unusable. The appropriate point during drying when the fixing step is initiated is at a point where the beads are wet, but without free liquid. In this stage, the beads appear as wetted sand.

Although the invention has been described in terms of specific embodiments and applications, persons skilled in the art can, in light of this teaching, generate additional embodiments without exceeding the scope or departing from the spirit of the practiced using other proteins which are similar to collagen to coat the polystyrene beads, such as laminin and fibronectin. Accordingly, it is to be understood that the description in this disclosure is proffered to facilitate comprehension of the invention, and should not be construed to limit the scope thereof.

What is claimed is:

1. A carrier arrangement for immobilizing anchorage-dependent cells, the arrangement comprising an autoclavable microsupport element having a core portion formed of a non-porous polystyrene having a density of approximately between 1.01 g/cc and less than 1.05 g/cc and a softening temperature of greater than 75° C., and a smooth surface layer portion formed of cross-linked collagen.

2. The arrangement of claim 1 wherein said microsupport element is a microcarrier bead which has a diameter between approximately 40 μm and 1000 μm.

3. The arrangement of claim 2 wherein said microcarrier bead has a diameter between approximately 90 μm and 250 μm.

4. The arrangement of claim 1 wherein said core portion has a density of approximately between 1.015 g/cc and 1.035 g/cc.

5. The arrangement of claim 1 wherein said polystyrene has a softening point above 80° C.

6. The arrangement of claim 1 wherein said polystyrene has a softening point above 100° C.

7. A smooth surface microcarrier bead formed in accordance with the process steps of:
coating a non-porous polystyrene core bead with collagen, said polystyrene having a density of approximately between 1.01 g/cc and less than 1.05 g/cc and a softening point of greater than 75° C.;
fixing said collagen coating to said polystyrene bead with a protein cross-linking agent, whereby the microcarrier bead is stable to washing and sterilization by autoclaving.

8. The microcarrier bead formed in accordance with the process steps of claim 7, wherein said process step of coating comprises the steps of:
suspending said polystyrene core bead in an acidic, aqueous collagen solution; and
evaporating said solution to a predetermined extent to form a collagen coating over said polystyrene core bead.

9. The microcarrier bead formed in accordance with the process steps of claim 8, wherein said acidic, aqueous collagen solution comprises 0.01 to 0.1N acetic acid.

10. The microcarrier bead formed in accordance with the process steps of claim 7 wherein said process step of fixing comprises the further step of suspending said collagen coated polystyrene core bead in a buffered saline solution containing a protein cross-linking agent.

11. The microcarrier bead formed in accordance with the process steps of claim 10 wherein said protein cross-linking agent comprises glutaraldehyde.

12. A smooth surface microcarrier bead formed in accordance with the process steps of
coating a non-porous core bead with a protein, said core bead being formed of a polystyrene having a density of approximately between 1.01 g/cc and less than 1.05 g/cc and a softening temperature of greater than 75° C.;
fixing said protein coating to said core bead, whereby the microcarrier bead is stable to washing and sterilization by autoclaving.

13. The microcarrier bead formed in accordance with the process steps of claim 12, wherein said protein is laminin.

14. The microcarrier bead formed in accordance with the process steps of claim 12, wherein said protein is fibronectin.

* * * * *